(12) United States Patent
Schrattenholz

(10) Patent No.: US 8,377,648 B2
(45) Date of Patent: Feb. 19, 2013

(54) AUTOIMMUNE REGULATION OF PROSTATE CANCER BY ANNEXIN A3

(75) Inventor: Andre Schrattenholz, Mainz (DE)

(73) Assignee: Proteosys AG, Mainz (DE)

( * ) Notice: Subject to any disclaimer, the term of this patent is extended or adjusted under 35 U.S.C. 154(b) by 414 days.

(21) Appl. No.: 12/595,678

(22) PCT Filed: Apr. 9, 2008

(86) PCT No.: PCT/EP2008/002802
§ 371 (c)(1),
(2), (4) Date: Oct. 13, 2009

(87) PCT Pub. No.: WO2008/125262
PCT Pub. Date: Oct. 23, 2008

(65) Prior Publication Data
US 2010/0129834 A1     May 27, 2010

Related U.S. Application Data

(60) Provisional application No. 60/911,329, filed on Apr. 12, 2007.

(51) Int. Cl.
*G01N 33/574* (2006.01)
(52) U.S. Cl. .................................. 435/7.23; 435/7.1
(58) Field of Classification Search ................ None
See application file for complete search history.

(56) References Cited

U.S. PATENT DOCUMENTS
2003/0108963 A1* 6/2003 Schlegel et al. ............. 435/7.23

FOREIGN PATENT DOCUMENTS
EP     1 724 586 A    11/2006
WO    2004/044590 A1   5/2004
WO    2006/125580 A1  11/2006

OTHER PUBLICATIONS

Carlsson et al, J Androl, 2004, 25:699-705.*
Harlow and Lane, Antibodies, a Laboratory Manual, Cold Spring Harbor Laboratory Press, 1988, p. 141-142.*
Ronquist et al, Prostate Cancer and Prostatic Dis, 2004, 21-31.*
Wozny et al., "Differential radioative quantification of protein abundance ratios between benign and malignant prostate tissues: . . . ", Proteomics, vol. 7, No. 2, Jan. 1, 2007, pp. 313-322.
Madoz-Gurpide et al., "Proteomics-based validation of genomic data: applications in colorectal cancer diagnosis", Molecular & Cellular Proteomics, vol. 5, No. 8, May 29, 2006, pp. 1471-1483.
Gerke, "Annexins and membrane dynamics", Biochimica et Biophysica ACTA. Molecular Cell Research, vol. 1357, No. 2, Jun. 27, 1997, pp. 129-154.
Li et al., "Proteomics-based identification of autoantibodies in the sera of healthy Chinese individuals from Beijing", Proteomics , vol. 6, No. 17, Sep. 2006, pp. 4781-4789.
Denzer et al, "Exosome: from internal vesicle of the multivesicular body to intercellular signaling device", Journal of Cell Science, vol. 113, pt 19, Oct. 2000, pp. 3365-3374.
Koellermann et al., "Expression and Prognostic Relevance of Annexin A3 in Prostate Cancer", European Association of Urology (on Line), Jan. 16, 2008.
Bastian, B. C. et al.: Autoantibodies to annexins: a diagnostic marker for cutaneous disorders? J Dermatol Sci. 1994; 8(3):194-202 (Abstract).
Cho-Chung, Y. S.: "Autoantibody biomarkers in the detection of cancer", Biochim Biophys Acta, Jun. 2006, 1762(6), pp. 587-591. 2006 (Abstract).
Miller, A. M. et al.: "CD4+CD25high T cells are enriched in the tumor and peripheral blood of prostate cancer patients", J Immunol., 2006, 177(10): 7398-7405.
Office Action in the corresponding Russian applcation No. 2009141703 dated Jan. 25, 2012 (5 pgs.).
Office Action in the corresponding Japanese application No. 2010-502455 dated May 2, 2012 (12 pgs.).

* cited by examiner

*Primary Examiner* — Misook Yu
*Assistant Examiner* — Mark Halvorson
(74) *Attorney, Agent, or Firm* — Rothwell, Figg, Ernst & Manbeck, P.C.

(57) ABSTRACT

The present invention relates to a method for the diagnosis of prostate carcinoma comprising the determination of annexin A3 (ANXA3) and/or autoantibodies against ANXA3 with a specific reagent. The method allows differentiation between benign, premalignant and malignant conditions. Further, the method has a prognostic relevance.

16 Claims, 5 Drawing Sheets

AUTOIMMUNE REGULATION OF PROSTATE CANCER BY ANNEXIN A3

CROSS REFERENCE TO RELATED APPLICATION

This application is a 35 U.S.C. 371 National Phase Entry Application from PCT/EP2008/002802, filed Apr. 9, 2008, which claims the benefit of U.S. Ser. No. 60/911,329 filed on Apr. 12, 2007, the disclosure of which is incorporated herein in its entirety by reference.

The present invention relates to a method for the diagnosis of prostate carcinoma comprising the determination of annexin A3 (ANXA3) and/or auto-antibodies against ANXA3 with a specific reagent. The method allows differentiation between benign, premalignant and malignant conditions. Further, the method has a prognostic relevance.

In a previous differential quantitative protein expression study it was shown that ANXA3 was significantly associated with prostate cancer (1). However, little is known about the role and biology of ANXA3 in the human prostate. So far it has been shown that ANXA3 is part of so-called exosomes, small vesicles released from a variety of epithelia (2), that these exosomes have a poorly understood role in regulation of the innate immune system (3), and that they have a very recently discovered anti-tumor activity (4). Recent reports have shown autoimmunity in prostate cancer patients against so-called prostasomes (5), which are exosomes from the prostate.

Protein biomarkers for therapy or diagnostics of prostate cancer and other epithelial cancers of urogenital tract are described in US 2005 130876, WO 03 086 461, WO 2005 078 124, EP 05 011 042.8 and EP 05 026 092.6. The content of these documents is herein incorporated by reference.

U.S. 60/812,089 and U.S. 60/859,489 disclose the diagnosis of cancer, wherein a sample is analyzed for the presence and/or amount of annexin A3 with highly specific monoclonal antibodies. The content of these documents is herein incorporated by reference.

Although ANXA3 has been known as a marker for prostate cancer, improved methods for differential diagnosis between benign, premalignant and malignant conditions are needed.

One of the aims of the present study was to investigate the expression and localization of ANXA3 in the epithelial components of benign prostate epithelium, high-grade prostatic intraepithelial neoplasia (HGPIN), and prostate cancer and to understand the differences and localisational changes in the course of prostatic transformation.

According to the present invention it was found that anti ANXA3-staining in benign prostate tissue is strong and apical, whereas in cancer it is weaker and more basal. A tissue array study with more than 1,900 cases shows that different patterns of ANXA3-expression in benign, premalignant and malignant prostate tissue have prognostic relevance and provide mechanistic understanding.

In advanced cancer, the presence of ANXA3 in nonepithelial interspersed cells was observed, which colocalize with a counterstain for regulatory T-cells (Tregs). Further, the presence of auto-antibodies against ANXA3 could be detected in cancer patients. These auto-antibodies against ANXA3 are probably induced under the oxidative stress of cancer cells. This provides evidence that ANXA3 release via exosomes constitutes a protective mechanism which cancer cells try to reverse by inducing autoimmunity against ANXA3-containing prostasomes in prostate cancer patients. Thus, the signalling of Tregs may be modulated by ANXA3 exosomes and/or cancer cells. Further, autoimmune antibodies against prostasomes/exosomes may be induced/regulated by ANXA3-positive T-cells.

Taken together there are strong indications that the release of ANXA3 to extracellular compartments of the prostate during benign prostatic hyperplasia (BPH) constitutes a defence mechanism against cancer and that cancerous tissue eventually turns this release down, by induction of autoimmune antibodies against ANXA3, and by a mechanism involving regulatory T-cells (Tregs). The different ANXA3-staining patterns also provide for the first time a possibility to predict PSA progression free survival in the intermediate risk group of patients stratified by Gleason scores, pT-stages and PSA.

In a first aspect, the present invention refers to a method for the diagnosis of cancer, preferably prostate cancer, wherein a tissue sample is analyzed for the intracellular distribution of annexin A3.

In a further aspect, the present invention refers to a method for diagnosing cancer, particularly prostate cancer, wherein a sample, e.g. a tissue or a body fluid sample, is analyzed for the presence, amount and/or intracellular distribution of annexin A3 and for an autoimmune response against annexin A3, wherein the autoimmune response is preferably characterized by the presence of auto-antibodies against annexin A3 and/or by the presence of regulatory T-cells.

A further aspect of the present invention refers to a method for the diagnosis of cancer, preferably prostate cancer, wherein a sample is analyzed for the presence and/or amount of auto-antibodies against annexin A3 and optionally for the presence and/or amount of regulatory T-cells.

Still a further aspect of the present invention refers to a method for the stratification of subjects which have been classified as having an intermediate risk of developing prostate cancer, wherein a sample from said subject is analyzed for the presence, localisation and/or amount of annexin A3.

Still a further aspect of the present invention is a test reagent for the diagnosis of cancer, particularly prostate cancer, comprising (i) a reagent for determining annexin A3 and (ii) a reagent for determining auto-antibodies against annexin A3 and/or a reagent for determining regulatory T-cells.

Still a further aspect of the present invention is a test reagent for the diagnosis of prostate cancer comprising a reagent for determining auto-antibodies against annexin A3.

The cancer which may be diagnosed according to the present invention is preferably a cancer of the urogenital and/or gastro-intestinal tract, such as cancer of prostate, bladder, kidney, urethra, ovaria, uterus or colon. Particularly, the cancer is an epithelial cancer. In an especially preferred embodiment, the cancer is prostate cancer.

In a preferred embodiment, the invention comprises a differential diagnosis of a disease stage and/or a prognostic evaluation. For example, the present invention allows a differential diagnosis of disease stages selected from:

(i) a benign condition, particularly a benign prostatic condition such as benign prostatic hyperplasia (BPH), fibrosis and chronic prostatitis, (ii) a premalignant condition such as prostatic intraepithelial neoplasia of various stages (PIN-1-3) including high-grade prostatic intraepithelial neoplasia (HGPIN), and/or (iii) a malignant condition such as prostate cancer, particularly advanced prostate cancer in a progressed state indicated by Gleason scores and/or pT-stages.

More preferably, the invention allows a differential diagnosis between a benign or premalignant condition on the one hand and a malignant condition on the other hand.

In a preferred embodiment of the invention, the presence, amount and/or distribution of ANXA3 is determined in a sample, which may be a body fluid or a tissue sample. More preferably, the sample is a tissue sample, e.g. a tissue section or biopsy, from prostate tissue. In a further embodiment, the intracellular distribution/localization of ANXA3 may be determined in a sample, wherein the sample is a tissue sample, preferably a tissue section or biopsy, e.g. from prostate tissue. Preferably, the intracellular localization of ANXA3 is determined in epithelial cells, particularly in prostate epithelial cells. It should be noted that presence, amount and intracellular localization may be determined on a single tissue sample or on different samples, e.g. a body fluid sample and a tissue sample from the same subject.

A high amount of ANXA3 in a sample, e.g. corresponding to a strong staining of a tissue sample, is primarily indicative for a benign condition. A moderate/low amount of ANXA3, e.g. corresponding to weak/moderate staining of a tissue sample, is indicative for a premalignant condition or to a early/early-intermediate stage malignant condition. The absence of ANXA3 in a sample is indicative for a malignant condition, primarily for a malignant condition in a progressed state, e.g. in an intermediate or late stage. Further, the absence of ANXA3 in a sample is indicative for an aggressive sub-group of prostate cancers, particularly with a high risk of progression after surgery, e.g. radical prostatectomy.

An apical intracellular localization of ANXA3, particularly the presence of ANXA3 in apically localized vesicles, e.g. exosomes and/or prostatosomes, is primarily indicative for a benign or premalignant condition. A diffuse intracellular localization of ANXA3, particularly in combination with the absence of apically localized vesicles, is indicative for a malignant condition.

The presence of an autoimmune response against ANXA3, e.g. the presence of auto-antibodies against ANXA3 and/or the presence of strong ANXA3-positive (but intracellular, not apical) regulatory T-cells, is primarily indicative for a malignant condition, particularly for a malignant condition in a progressed state.

The present invention encompasses determination of polypeptides or cells in a sample. Preferably, this determination comprises immunological methods, wherein the presence, amounts and/or localization of a component as determined using immunological test reagents.

The reagent for determining ANXA3 in a sample is preferably an antibody which is specific for ANXA3, e.g. a polyclonal or a monoclonal antibody. Especially preferred are highly specific monoclonal antibodies as described in U.S. 60/812,089 and U.S. 60/859,489, which are herein incorporated by reference.

The reagent for determining ANXA3 auto-antibodies in a sample is preferably an ANXA3 polypeptide or a fragment thereof comprising epitopes recognized by auto-antibodies. More preferably, the ANXA3 polypeptide is a recombinant ANXA3 polypeptide.

The reagent for determining regulatory T-cells in a sample is preferably an antibody directed against a marker for regulatory T-cells, e.g. CD25 or Foxp3 or other such markers.

The method of the present invention may be carried out in any test format suitable for immunological determinations, including test formats suitable for automated devices. In some test formats it may be preferred to use a reagent which carries a labelling group, e.g. a visual marker, such as a latex or gold bead, a fluorescence marker group, an enzymatic marker group etc. Conjugates of reagents and labelling groups may be produced according to standard methods, e.g. by covalent coupling to reactive amino acid side groups of the reagent such as carboxy, amino and/or thiol groups with labelling groups, e.g. via bifunctional spacer molecules.

The sample is preferably obtained from a human subject. In some embodiments, the method is a non-invasive diagnostic procedure, wherein the sample may be e.g. a urine sample, particularly an exprimate urine sample or a faeces sample. If desired, the sample may be subjected to pretreatment procedures, e.g. gel filtration. In further embodiments, the method may be a histochemical procedure wherein the sample may be a tissue sample, particularly a biopsy, e.g. a punch or lance biopsy or a sample from TUR-P (trans urethral resection of the prostate). In a histochemical procedure, a selective determination of intracellular or extracellular ANXA3 may be carried out by determining the localisation of ANXA3 within the sample.

In a preferred embodiment, the invention comprises a semi-quantitative or quantitative determination of ANXA3. This semi-quantitative or quantitative determination may involve evaluation of test results based on predetermined cut-off values and correlating the results of the evaluation with a disease stage. Cut-off values may be determined by determining ANXA3 in samples from healthy persons and/or persons with a predetermined disease stage according to known methods. Further, the amount of ANXA3 in a sample may also be determined by evaluation of stained tissue samples and correlating the results of the evaluation with a disease stage.

The present invention also refers to the determination of an autoimmune response, e.g. of auto-antibodies directed against ANXA3 and/or the presence of regulatory T-cells. This determination may be carried out individually or in combination with the determination of ANXA3. The presence of auto-antibodies is indicative for a malignant condition, particularly a malignant condition in a progressed stage. The determination of auto-antibodies is optionally combined with a determination of regulatory T-cells. The presence of regulatory T-cells is indicative for a malignant condition, particularly a malignant condition in a progressed stage.

The sample may be subjected to a fractionation procedure which allows separate determination of extracellular and intracellular ANXA3. For example, the sample may be centrifuged in order to obtain a cell pellet and a supernatant whereby intracellular annexin A3 is determined in the cell pellet and extracellular annexin A3 is determined in the supernatant. In an especially preferred embodiment the method comprises a selective determination of extracellular ANXA3. In a further especially preferred embodiment, the method comprises a selective determination of intracellular ANXA3.

The method of the present invention may additionally comprise the determination of further cancer markers, e.g. cancer markers. The determination of further markers may be carried out in the same sample where ANXA3 is determined or in different samples, e.g. blood, serum and/or plasma samples. Especially preferred is the determination of blood, serum or plasma markers, in particular of at least one member of the kallikrein protease family, such as prostate specific antigen (PSA) and/or at least one epithelial cell marker, particularly prostate specific membrane antigen (PSMA).

The present invention may be a screening procedure, wherein an individual or a group of individuals are tested for cancer, particularly prostate cancer. On the other hand, the method may also comprise a prognostic evaluation or therapeutic follow-up testing, wherein an individual who already has been diagnosed positive for cancer, particularly prostate cancer or a precursor stage thereof, is subjected to a prognostic evaluation and/or a therapy control monitoring.

In an especially preferred embodiment, the invention relates to a prognostic evaluation of the disease progression, which is a valuable tool in any diagnostic assessment, particularly for therapy control. The prognostic evaluation may be based on determination of ANXA3 alone or in combination with other markers such as PSA. For example, by histological evaluation and/or by measuring levels of PSA or further cancer markers, patients may be classified in a low risk group (e.g. PSA level .ltoreq.10 ng/ml), an intermediate risk group (e.g. PSA level>10 and <20 ng/ml) and a high risk group (e.g. PSA level 20 ng/ml). Determination of ANXA3 in these patient groups may lead to further valuable information, particularly in patients having been classified as being in an intermediate risk group. If these intermediate risk patients are ANXA3 positive, the percentage of PSA-free survival is significantly higher than in patients having been determined as being negative for ANXA3. Thus, the invention allows a further risk stratification for individual patient groups. Preferably, patients in a group having originally been classified as being in an intermediate risk group, may be reclassified based on the results of the ANXA3 determination. Patients who are ANXA3 positive may be reclassified as being in a low risk group and patients who are ANXA3-negative (and optionally have an autoimmune response against ANXA3) are classified as being in a high risk group.

Further, the present invention shall be explained in more detail by the following Figures and Examples.

EXAMPLE

1. Materials and Methods 1.1 Antibody

Figure 1:
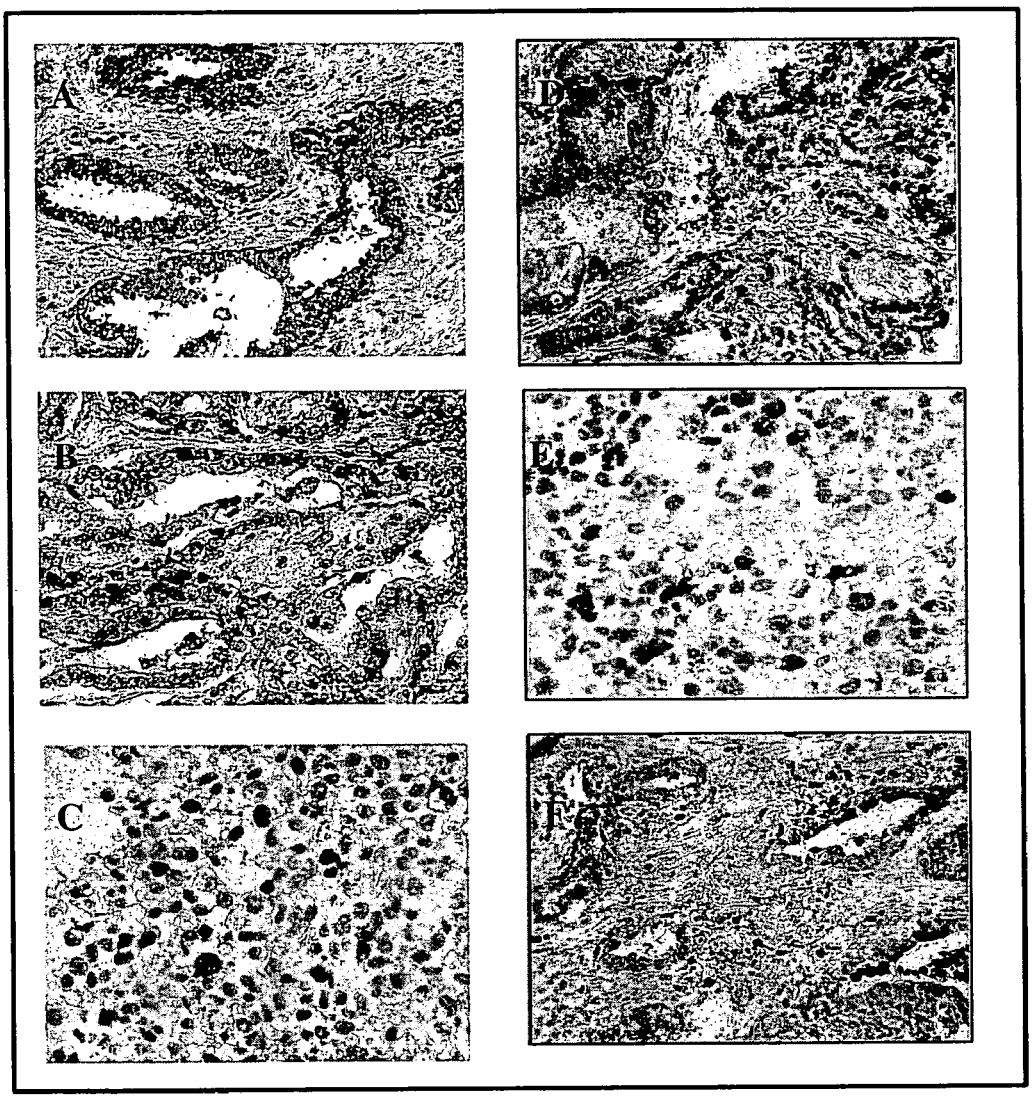
FIG. 1 shows the difference of ANXA3 staining intensity and localization in a benign prostatic hyperplasia sample (1A), a sample from prostate cancer tissue with intermediate Gleason score (1B), and a tissue section of advanced cancer with ANXA3 positive interspersed cells (1C). This type of cell also stains positive for CD3 (general T-cell marker, 1D); as well as for CD25 a specific marker for regulatory T-cells (Tregs, 1E) and for Foxp3 another specific marker for Tregs (1F).

The following antibody was used in this study:
Clone tgc7 ProVII5C5 (DSM ACC2780), monoclonal, 2.4 mg/ml; directed against the target protein ANXA3.

1.2 Tissues

A preexisting prostate cancer TMA containing >3000 tissue samples was analyzed. A detailed description of the composition is provided in the results section.

1.3 Immunohistochemistry (IHC)

An IHC protocol suitable for annexin A3 detection in formalin fixed tissues was developed. The detailed protocol is given below.

ANXA3 Immunostaining (IHC) Protocol

Slide Preparation
  deparaffinize TMAs at least 1 h in Xylene, GFS 2×5 min Xylene
  rehydrate in descending ethanol series up to Aqua dest
  rinse 5 minutes in PBS buffer
Pretreatement (Epitope Retrieval)
  autoclave slides for 5 min in acetic acid pH2 rinse 5 minutes in PBS buffer
Peroxidase-Blocking
  incubate 10 min in 1% $H_2O_2$/Methanol
  rinse 2×5 min in PBS buffer
Antibody Incubation
  dilute primary antibody (ANXA3) 1:8100 (0.3 µg/ml) in PBS
  cover tissue/TMA section with 100-200 µl diluted antibody
  incubate 2 h at 30° C. in moist chamber
  rinse 2×5 min in TRIS-PBS buffer (1:10)
  apply HRP-conjugated second antibody (EnVision DAKO K4003, anti rabbit) for 30 min at 30° C.
  rinse 2×5 min in TRIS-PBS buffer
Chromogen
  cover slides for 10 min with DAB-Chromogen (Liquid DAB DAKO Code No.: K 3467) at room temperature
  wash slides in PBS-Buffer thoroughly
  counterstain for 1 min sec with hematoxylin (Harris Hamatoxylin HTX 31000, Medite GmbH)
  rinse with water
  differentiate in HCl-Ethanolblue for 5 min in water ascending ethanol series
  xylenecover 1.4 IHC Scoring One pathologist evaluated all stainings. Version a) For each tissue sample and antibody, the membranous staining intensity was estimated by visual inspection in a four step scale (0, 1, 2, 3). In addition the fractions of tumor cells staining positive was estimated in a 4 step scale (<20%, >=20<40%, >=40-<90%, >90%). A final IHC score was built from these two parameters.

Score Definition

| Score | Definition |
|---|---|
| negative | Int 0 |
| weak | Int 1 in ≦40% of tumor cells or |
|  | Int 2 in ≦20% of tumor cells |
| moderate | Int 1 in >40% of tumor cells or |
|  | Int 2 in >20 ≦ 90% of tumor cells or |
|  | Int 3 in <40% of tumor cells |
| strong | Int 2 in ≧90% of tumor cells or |
|  | Int 3 in ≧40% of tumor cells |

For certain statistical analyses cancers were grouped as negative (negative) or positive (weak, moderate, strong)

1.5 Datafile Description

All data generated in this study are summarized in a data file with field descriptions as follows:

| Field name | Explanation |
|---|---|
| TMA block No | TMA coordinate |
| localisation | TMA coordinate |
| PSA | Preoperative PSA (ng/ml) |
| pT | pT stage |
| pN | Histopathological lymph node status |
| Gleason pattern | Gleason grading (pattern) |
| Gleason Score | Gleason grading (score) |
| Risk group | Risk category classified as low, intermediate and high |
| relapse | PSA relapse |
| months fol-up |  |
| ANXA3 % PCA | fraction of stained prostate cancer cells (PCA) |
| ANXA3 Int PCA | staining intensity (0-3) |
| ANXA3 score PCA | IHC result. For definition see 2.4 |
| ANXA3 pattern PCA | Staining pattern defined as diffuse cytoplasmic (diffuse) vs. apical accentuated cytoplasmic (apical) staining |
| comb. score/pattern | Combined score including IHC score and staining pattern |
| ANXA3 % PIN | fraction of stained PIN cells |
| ANXA3 Int PIN | staining intensity (0-3) |
| ANXA3 score PIN | IHC result. For definition see 2.4 |
| ANXA3 pattern PIN | Staining pattern defined as diffuse cytoplasmic (diffuse) vs. apical accentuated cytoplasmic (apical) staining |
| ANXA3 % benign | fraction of stained benign cells |
| ANXA3 Int benign | staining intensify (0-3) |
| ANXA3 score benign | IHC result. For definition see 2.4 |
| ANXA3 pattern benign | Staining pattern defined as diffuse cytoplasmic (diffuse) vs. apical accentuated cytoplasmic (apical) staining |

1.6 Statistics

Chi square test was employed to calculate the probability of ANXA3 expression differences between different tumor subsets. Kaplan-Meier plots were calculated to address the impact of ANXA3 expression on patient prognosis. For multivariate analysis Cox regression analysis was performed.

2. Results

Based on the analysis of a tissue microarray containing cancer cores of 1679 radical prostatectomy-derived specimens, the representative images from immunocytochemistry with a specific antibody against ANXA3 (FIG. 1) show a difference of ANXA3 staining intensity and localization in typical specimens of benign prostatic hyperplasia (1A), prostate cancer tissue with intermediate Gleason score (1B) and advanced cancer (1C). In addition a set of 135 benign and 125 preneoplastic lesions (high grade PIN) was analyzed.

In general ANXA3 staining was predominantly cytoplasmic and showed an intracellular differentiation with a cytoplasmic and membrane bound/vesicular pattern. In benign glandular epithelium a prominent cellular and nuclear ANXA3 staining was seen. In addition, staining was found in small cytoplasmic vesicles, which were concentrated at the apex of the cell, resulting in an apically accentuated cytoplasmic staining pattern. At the cell apex the formation of ANXA3 positive vesicles was frequently observed corresponding to an apocrine secretion process into the glandular ducts.

Figure 2:
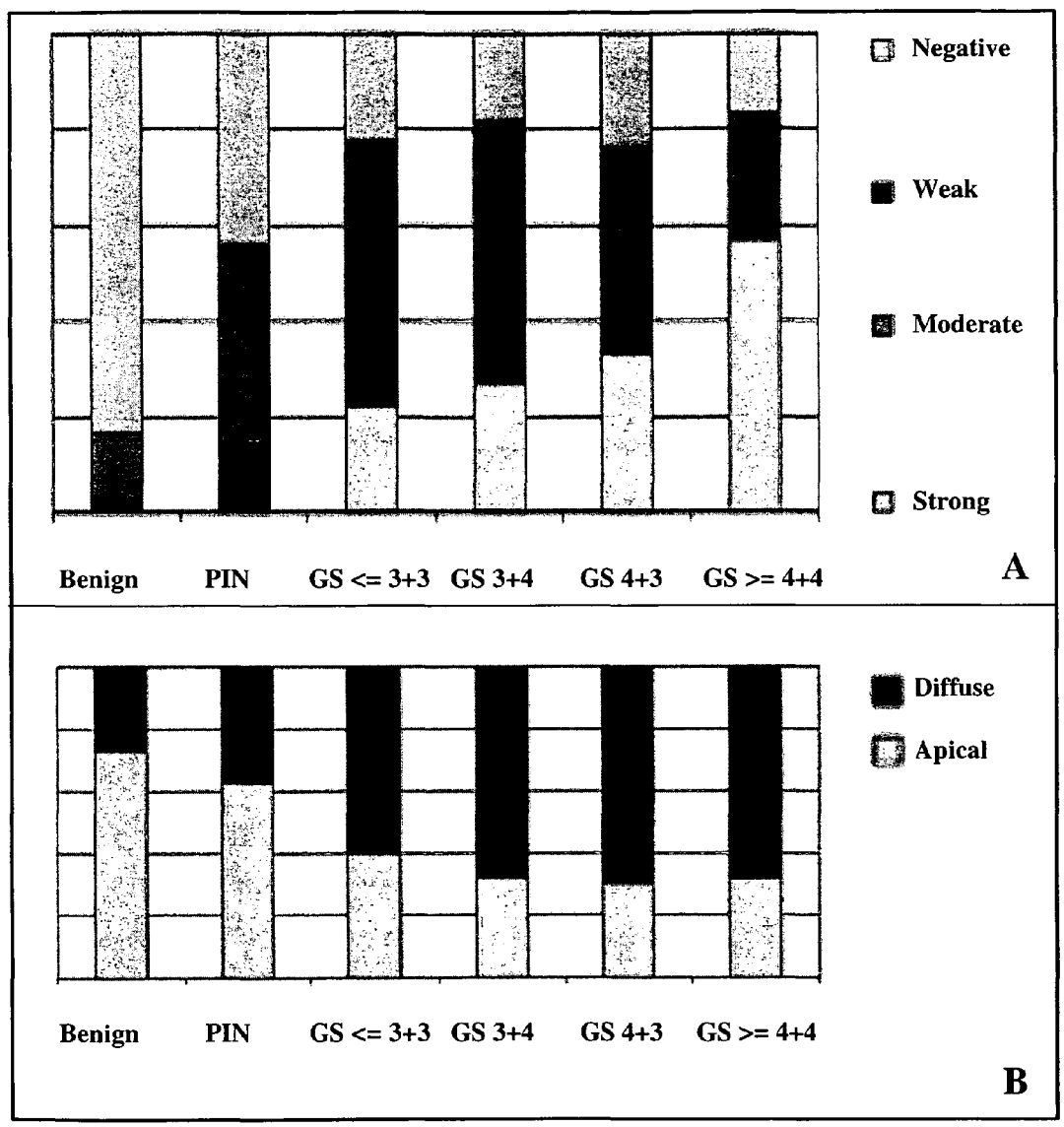
FIG. 2 shows a summary of ANX staining results (negative, weak, moderate, strong) depending on the respective condition (benign condition, premalignant condition PIN and malignant condition), i.e, cancer classified according to Gleason (GS) score: Highest staining intensity was found in benign epithelium.
(a) Staining intensity decreased in PIN and carcinoma with increasing dedifferentiation.
(b) Apical ANXA3 staining is inversely correlated with increasing severity of cancer. The correlation of both parameters with the various stages of prostatic transformation are highly significant, with .rho. values of <0.001. ANXA3, annexin A3; PIN, prostatic intraepithelial neoplasia.

Benign secretory cells and HGPIN lesions uniformly stained positive mostly with an apical accentuated cytoplasmic staining. However in HGPIN, staining intensity significantly decreased ($p<0.0001$). In cancer staining intensity further significantly decreased (including negative staining in 27%, $p<0.0001$) and a clear shift from the apical accentuated cytoplasmic staining pattern to a diffuse cytoplasmic staining was observed ($p<0.0001$). A summary of these results is provided in FIG. 2.

Negative ANXA3 staining was associated with pT-stage and Gleason score ($p<0.0001$) but not with PSA ($p=0.29$). Kaplan-Meier analysis revealed a significantly reduced PSA progression free survival ($p<0.0001$; log rank test). In multivariate analysis, negative ANXA3 staining was shown to be an independent prognostic predictor (HR 1.20, $p=0.002$). Details are provided in Tables 1 and 2.

The further analysis of interspersed single cells in advanced cancer by antibody-staining showed that these cells are predominantly T-cells (1D) and more specifically regulatory T-cells (Tregs) because they express CD25 (1E) and Foxp3 (1F) (6). Tregs have recently been reported to contribute to tumor-specific tolerance (7).

Concerning the analysis of ANXA3-positive cancers, there is a correlation for Gleason score ($p=0.04$), however counter to expectations high grade cancers showed the largest proportion of strongly stained cancers (35.6%) and the proportion of weakly stained cancers was almost identical in low and high grade cancers (35.6 vs 36.3%). Staining intensity also correlated with PSA level ($p=0.0029$). Cancers strongly stained for ANXA3 were most frequently found in the PSA≧20 ng/ml category (41.1%), a weak staining for ANXA3 was most frequently found in the PSA categories below 20 ng/ml. There was a trend for a decreased staining intensity in locally advanced cancers, however this did not reach statistical significance ($p=0.0630$).

PSA follow up was available in 1317 patients. Biochemical relapse was defined as PSA>=0.1 ng/ml on two consecutive measurements. 354 patients developed PSA relapse. Median overall follow up was 33 months Median follow up of the non relapsing patients was 39 months. Performing a ANXA3—univariate analysis, we could show that negative staining for ANXA3 was associated with a significantly decreased PSA free survival time compared to ANXA3 positive tumors ($p<0.0001$). Subanalysis of the ANXA3 positive tumors with respect to the staining pattern was able to further separate this group of patients into two prognostically relevant subgroups. Prognosis was significantly worse in ANXA3 positive tumors with a diffuse epithelial staining compared to their apical stained counterparts (log rank test $p=0.0013$, FIG. 3A).

To further investigate whether ANXA3 status has prognostic relevance in addition to the combined use of the well established classic prognostic parameters PSA, Gleason grade and pT-stage, we divided our cohort into 3 risk groups. According to PSA, Grade and stage patients were categorized at low, intermediate and high risk of progression. In those at low risk for progression preoperative PSA was 10 ng/ml, or less, Gleason score of the prostatectomy specimen was 6 or less and cancer was organ confined. In those at high risk for progression preoperative PSA was greater than 20 ng/ml, Gleason score of the prostatectomy specimen was 7 or greater and tumour stage was $\geq$pT3. Those not at low or high risk were assigned to an intermediate risk group.

Figure 3:
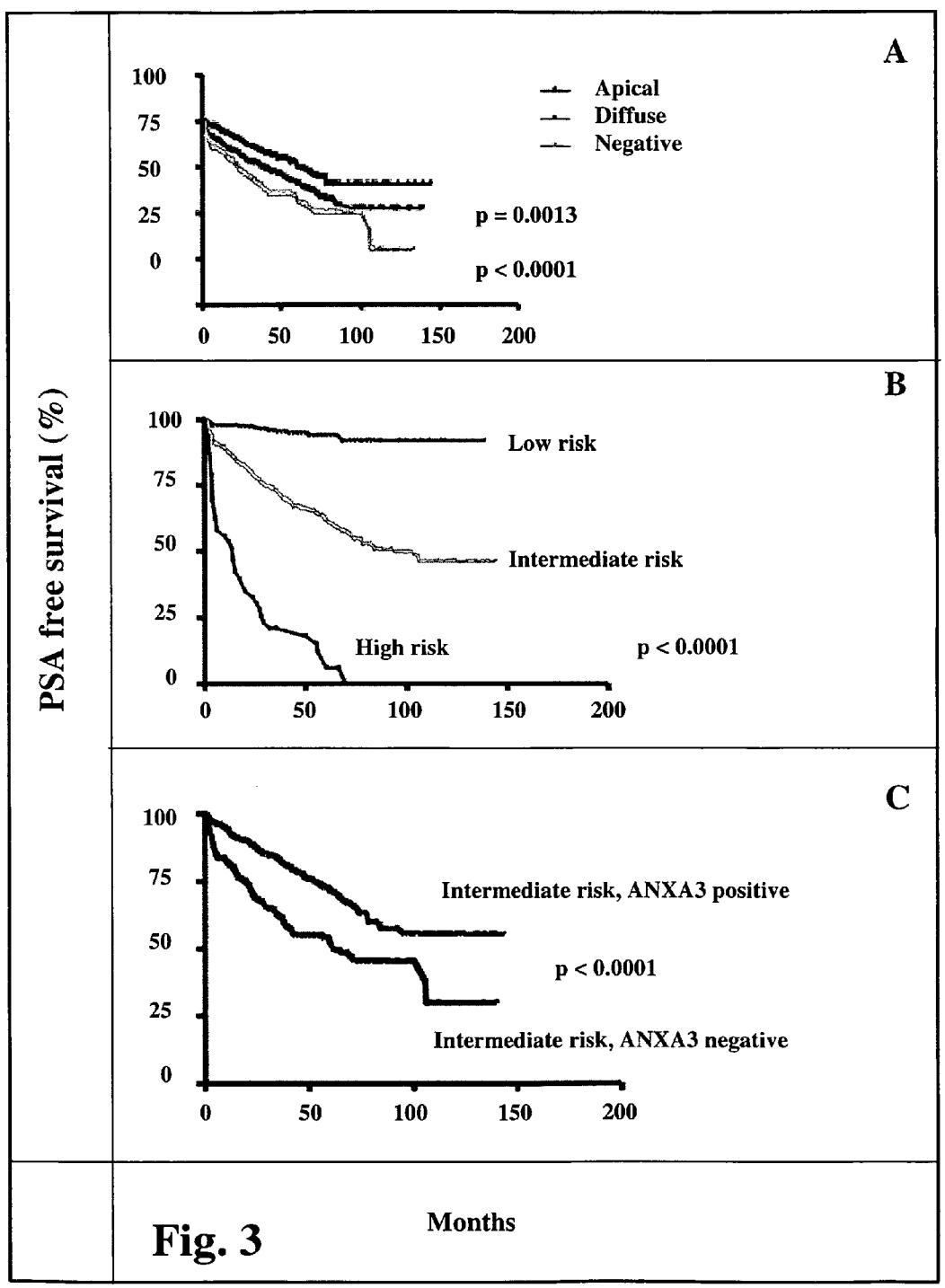
FIG. 3 shows the association of PSA-free survival time with ANXA3 staining in different patient groups.
(a) Subanalysis of ANXA3 positive tumors with respect to the staining pattern apical vs. diffuse enabled separation into prognostically relevant subgroups.
(b) Probability of PSA progression-free survival according to risk group classification.
(c) Substratification by ANXA3 status (positive vs. Negative) enabled separation of the intermediate-risk group, which represents the largest cohort (n=969), into a high- and a low-risk subgroup (.rho.=0.0001). ANXA3, annexin A3; PSA, prostate-specific antigen.

As shown in FIG. 3B, risk categories showed significant different risk of progression (p<0.0001). Substratification by ANXA3 status (positive vs. negative) was able to separate the intermediate risk group, which represents the largest cohort (n=922), into a high and a low risk subgroup (p=0.0001). No subgroups could be defined in the low or high risk group (Table 3). Kaplan-Meier analysis of the intermediate risk also showed significantly decreased PSA PFS for the ANA3 negative patients (FIG. 3C).

Negative staining for ANXA3 was associated with a significantly decreased PSA-free survival time compared with ANXA3-positive tumors ($\rho$<0.0001, FIG. 4A). Stratification of the ANXA3-positive cancers for the staining score (weak vs. moderate vs. strong) however failed to show prognostic relevant subgroups (log-rank test, $\rho$=0.642, data not shown). Beside ANXA3 staining (negative vs. Positive), univariate analysis also showed prognostic significance for the established prognostic factors Gleason score, pT stage, and preoperative PSA serum level (p<0.0001, FIG. 4B-D).

Figure 4:
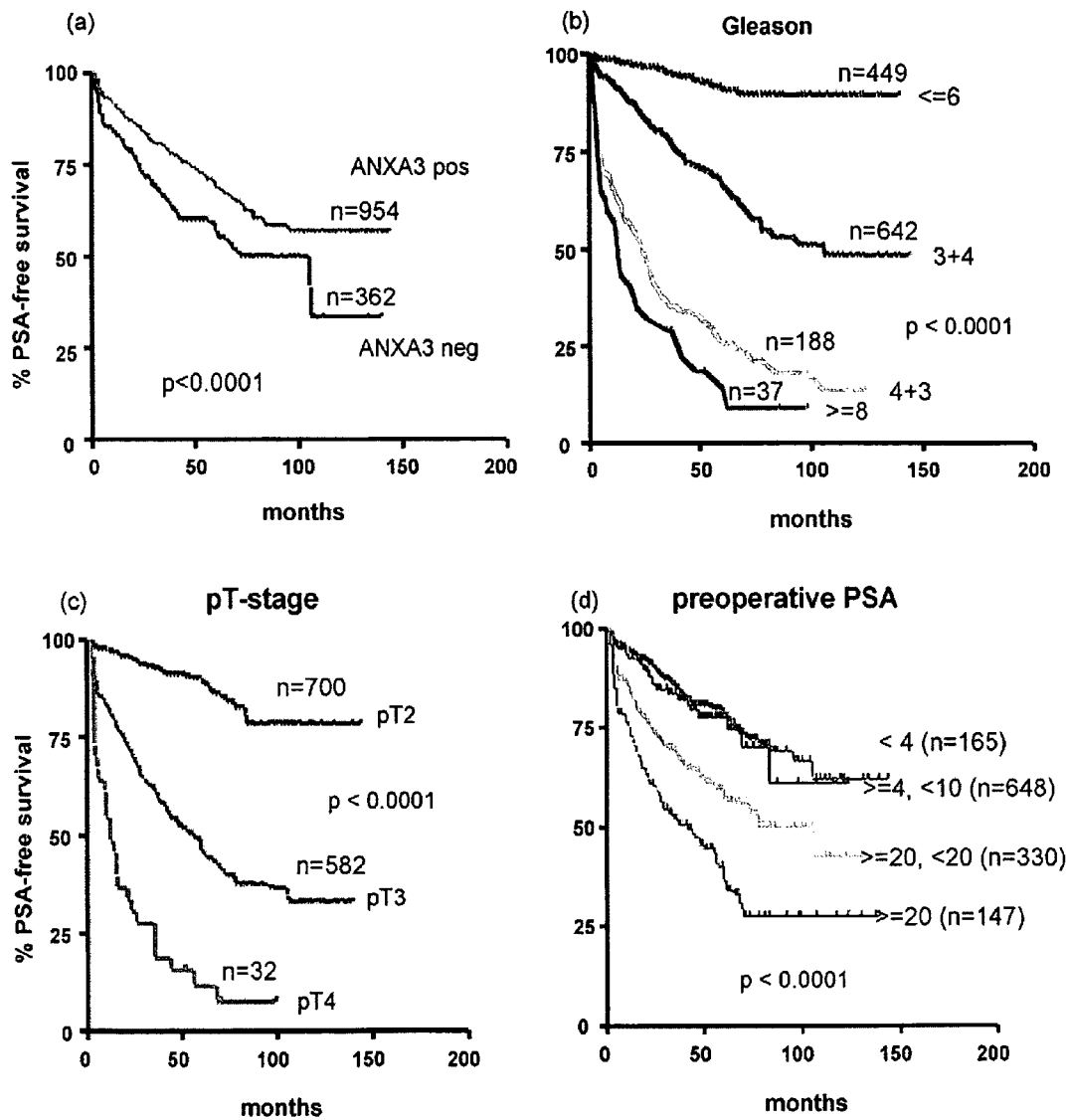
FIG. 4 shows the association of PSA free survival time with the ANXA3 status. Negative ANXA3 staining status is significantly correlated with PSA-free survival. Probability of PSA-free survival according to (b) Gleason grade, (c) pT stage, and (d) preoperative PSA (in ng/ml). ANXA3, annexin A3; PSA, prostate-specific antigen.
Figure 5:
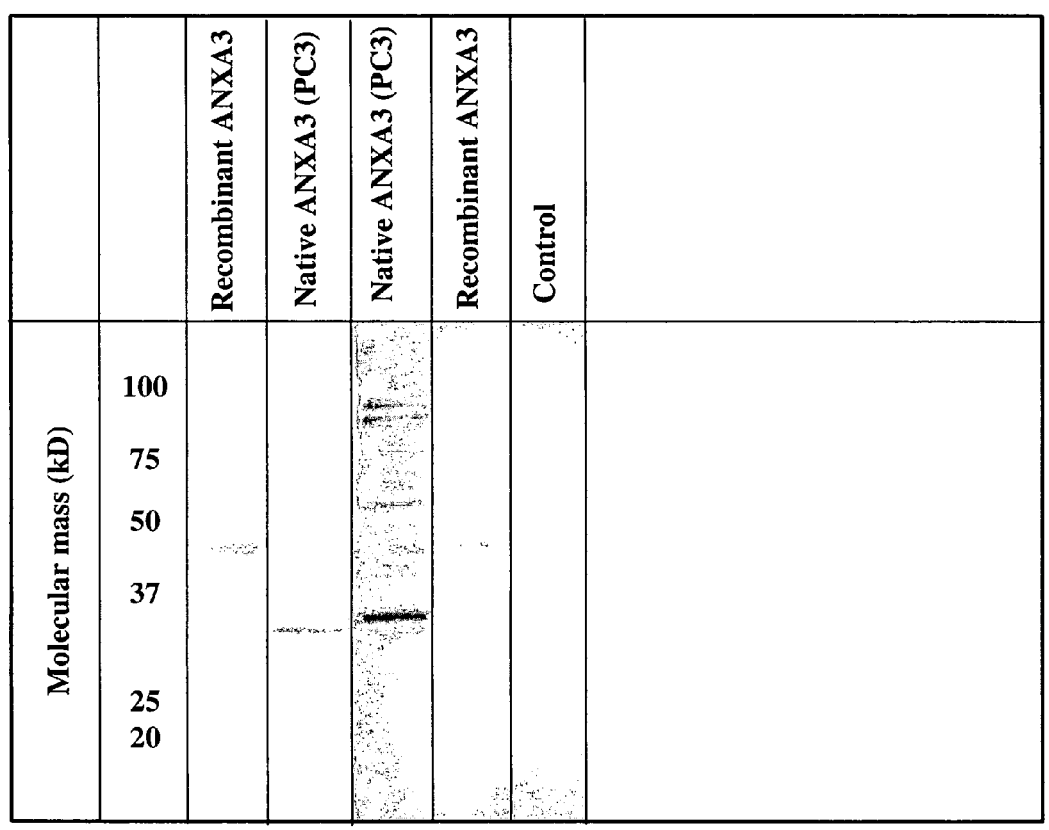
FIG. 5 shows the presence of auto-antibodies in the serum from a prostate cancer patient.

We proceeded to test the possibility of antiANXA3-autoimmunity in cancer patients, by screening patient sera for immune reactivity against recombinant ANXA3 in a sandwich-ELISA. Controls included ANXA5, MCV, Ana, with and without phosphoserine coating. Indeed we found a very high and specific anti-ANXA3 titer in some prostate cancer patients. As shown in FIG. 4, the polyclonal serum of one of these patients stains recombinant ANXA3, native ANXA3 from a prostate cancer cell line (PC3 cells), as compared with the staining with a corresponding monoclonal anti-ANXA3 antibody. Isolating B-cells from the whole blood of this patient, and using our specific monoclonal antibody, recombinant ANXA3 and PC3-cell extracts as positive controls, we were able to isolate and cultivate the corresponding anti-ANXA3 antibody producing B-cell clones and thus to proceed to a human monoclonal anti-ANXA3 antibody. The corresponding Western blots are shown in FIG. 5.

3. Discussion

The consistent changes in localization and intracellular distribution of ANXA3 during the transition from benign to malignant prostate epithelium and its prognostic significance suggest an important role of ANXA3 in prostate tissue biology. The presence of secreted ANXA3 in the extracellular compartment of the prostate, in line with the reported presence of the protein in exosomes/prostasomes (2) and the proposed anti-cancer activity of these vesicles (4) led us to test whether ANXA 3 is accessible with antibodies in urine or PC3 cell extracts from prostate cancer patients. A FACS analysis showed indeed that ANXA3 is a potentially antigenic surface protein (data not shown). Screening sera from cancer and BPH-patients (from a large scale clinical study evaluating the diagnostic value of ANXA3), we found auto-antibodies in a small set of cancer patients and isolated the corresponding clones of anti-ANXA3 antibody producing B-cells.

On the background of deficiencies of the current standard biomarker for early prostate cancer detection, PSA (8, 9), and with regard to the difficult decisions concerning risk assessment using biopsies, or specimens after total prostectomy (10, 11), ANXA3 offers the potential of a comprehensive diagnostic protein biomarker.

One of the key features of ANXA3 is that the intra- and extracellular distributions and localizations enable not only a stable, non-invasive detection in a body fluid for early detection of prostate cancer, but also reflect an important aspect of tumor biology, which is not accessible by DNA/RNA analytics (which principally only can detect surrogates of total ANXA3).

Our results are consistent with an anti-cancer and protective role of ANXA3 secreted from prostatic epithelium of BPH, probably in exosomes/prostasomes, which is gradually lost during prostatic transformation from BPH via PIN, towards higher Gleason-scored prostate cancer. The reduction of exosomal ANXA3 is due to an autoimmune mechanism triggered in advanced cancers by regulatory T-cells, aimed at surface antigens of extracellular prostasomes.

For the first time the large group of patients in the intermediate risk group can be further profiled and it will be of great interest to follow-up future, ANXA3-based prediction of prostate cancer progression. Given this molecular background of ANXA3 in prostate cancer (1) and implying a role in immune regulation of prostatic transformation to cancerous stages, the role of ANXA3 in membrane trafficking, lymphocyte migration, cell motility and signal transduction (12), its presence in exosomes (2) and in prostasomes (13) is of particular interest. Prostasomes are considered to regulate the innate immune system (14, 15) and moreover have recently been associated with different stages of prostate cancer (5, 16).

Correlation of tissue and urinary ANXA3 could further help to understand the cancer-related kinetics of localization and release of ANXA3. There is a possibility that the discovery of ANXA3 as marker for prostate cancer presented here has more general implications, because two very recent reports found ANXA3 as inversely correlated marker similar to our study for ovarian clear cell adenocarcinoma (17) and colorectal cancer (18, 19). So the hypothesis that ANXA3 release plays a general cancer-related role for epithelial adenocarcinomas deserves additional attention.

Negative staining for ANXA3 being an independent prognostic factor in prostate cancer represents the most important finding of our study. Negative staining for ANXA3 characterizes a biologically aggressive subgroup of prostate cancers with a high risk of progression after radical prostatectomy. In conclusion, ANXA3 represents a promising candidate tissue marker, which, when combined with the standard prognostic parameters, is suggested to provide a more precise prediction of prognosis in the individual patient and therefore to contribute to future patient management.

Tables:

TABLE 1

ANXA3 staining in benign, premalignant (PIN) and malignant prostate epithelium

| | | Benign | | PIN | | PCA | | |
|---|---|---|---|---|---|---|---|---|
| | | n | % | n | % | n | % | P |
| Staining intensity | negative | 0 | 0.0 | 0 | 0.0 | 431 | 27.1 | <0.0001 |
| | weak | 3 | 2.2 | 18 | 14.4 | 444 | 27.9 | |
| | moderate | 20 | 14.8 | 52 | 41.6 | 393 | 24.7 | |
| | strong | 112 | 83.0 | 55 | 44.0 | 324 | 20.3 | |
| | n total (%) | 135 | 100.0 | 125 | 100.0 | 1592 | 100.0 | |

TABLE 1-continued

ANXA3 staining in benign, premalignant
(PIN) and malignant prostate epithelium

| | | Benign | | PIN | | PCA | | |
|---|---|---|---|---|---|---|---|---|
| | | n | % | n | % | n | % | P |
| Staining pattern | apical | 96 | 72.7 | 77 | 62.6 | 405 | 34.9 | <0.0001 |
| | diffuse | 36 | 27.3 | 46 | 37.4 | 756 | 65.1 | |
| | n total (%) | 132 | 100.0 | 123 | 100.0 | 1161 | 100.0 | |

TABLE 2

Correlation of ANXA3 staining with
pT-stage, Gleason score (GS) and PSA

| | | staining negative | | staining positive | | total | total | |
|---|---|---|---|---|---|---|---|---|
| | | n | % | n | % | n | % | p |
| PT | 2 | 199 | 22.0 | 706 | 78.0 | 905 | 100 | <0.0001 |
| | >=3 | 232 | 33.6 | 458 | 66.4 | 690 | 100 | |
| | total | | | | | 1595 | | |
| GS | <3 + 3 | 128 | 22.3 | 447 | 77.7 | 575 | 100 | <0.0001 |
| | 3 + 4 | 208 | 27.1 | 559 | 72.9 | 767 | 100 | |
| | >=4 + 3 | 95 | 37.3 | 160 | 62.7 | 255 | 100 | |
| | total | | | | | 1597 | | |
| PSA | <4 | 66 | 30.6 | 150 | 69.4 | 216 | 100 | 0.2878 |
| | >=4 > 10 | 226 | 28.0 | 580 | 72.0 | 806 | 100 | |
| | >=10 < 20 | 99 | 25.6 | 287 | 74.4 | 386 | 100 | |
| | >20 | 36 | 22.5 | 124 | 77.5 | 160 | 100 | |
| | total | | | | | 1568 | | |

TABLE 3

Risk stratification dividing patients into those at low,
intermediate and high risk for progression showing biochemical
relapse rate according to ANXA3 status

| | ANXA3 | PSA relapse free | | PSA relapse | | |
|---|---|---|---|---|---|---|
| Risk group | status | n | % | n | % | p |
| low | neg | 65 | 95.6 | 3 | 4.4 | 1.00 |
| | pos | 226 | 95.4 | 11 | 4.6 | |
| intermediate | neg | 178 | 46.4 | 106 | 53.6 | <0.0001 |
| | pos | 492 | 77.1 | 146 | 22.9 | |
| high | neg | 1 | 9.1 | 10 | 90.9 | 1.00 |
| | pos | 2 | 6.25 | 30 | 93.75 | |

REFERENCES

1. W. Wozny et al., *Proteomics*. 7, 313 (2007).
2. T. Pisitkun, R. F. Shen, M. A. Knepper, *Proc Natl Acad Sci USA* 101, 13368 (2004).
3. S. Keller, M. P. Sanderson, A. Stoeck, P. Altevogt, *Immunol. Lett.* 107, 102 (2006).
4. Y. Yang et al., *J Cancer Res. Clin. Oncol.* (2007).
5. M. Schostak, A. Schrattenholz, submitted (2007).
6. A. Larsson et al., *Urol. Oncol.* 24, 195 (2006).
7. M. Miyara, S. Sakaguchi, *Trends Mol. Med.* (2007).
8. G. Zhou, H. I. Levitsky, *J Immunol.* 178, 2155 (2007).
9. A. W. Roddam et al., *Eur. Urol.* 48, 386 (2005).
10. A. Stamey et al., *J. Urol.* 172, 1297 (2004).
11. M. Amin et al., *Scand. J. Urol. Nephrol. Suppl* 20 (2005).
12. J. I. Epstein et al., *Scand. J Urol. Nephrol. Suppl* 34 (2005).
13. V. Gerke, C. E. Creutz, S. E. Moss, *Nat. Rev. Mol. Cell Biol.* 6, 449 (2005).
14. F. G. Kravets et al., *Prostate* 43, 169 (2000).
15. J. Radons, G. Multhoff, *Exerc. Immunol. Rev.* 11, 17 (2005).
16. N. E. Schartz, N. Chaput, F. Andre, L. Zitvogel, *Curr. Opin. Mol. Ther.* 4, 372 (2002).
17. A. J. Abusamra et al., *Blood Cells Mol. Dis.* 35, 169 (2005).
18. A. Morita et al., *Proteomics*. (2006).
19. P. Alfonso et al., *Proteomics*. 5, 2602 (2005).
20. J. Madoz-Gurpide et al., *Mol. Cell Proteomics*. 5, 1471 (2006).

The invention claimed is:

1. A method for the diagnosis of prostate cancer comprising analyzing a tissue sample to determine intracellular distribution of annexin A3 and diagnosing a pre-malignant or malignant prostate condition if the analysis is characterized by a diffuse intracellular localization of annexin A3 staining of said tissue sample compared to diagnosing a benign prostate condition where intracellular apical annexin A3 staining is detected in said tissue.

2. The method of claim 1 wherein the annexin A3 is detected in said sample using a reagent that is an antibody.

3. The method of claim 2, wherein the antibody is a monoclonal antibody.

4. The method of claim 1 which is a histochemical procedure.

5. The method of claim 4 wherein the sample is a tissue sample.

6. The method of claim 1, wherein the intracellular distribution of annexin A3 is determined in epithelial cells.

7. The method of claim 1 comprising a differential diagnosis of disease stages selected from:
 (i) a benign condition,
 (ii) a premalignant condition, and
 (iii) a malignant condition.

8. The method of claim 1 wherein at least one further marker is determined.

9. The method of claim 8 wherein the further marker is prostate-specific antigen (PSA) and/or prostate specific membrane antigen (PSMA).

10. The method of claim 1 wherein further auto-antibodies against annexin A3 are determined.

11. A method for the diagnosis of prostate cancer, comprising analyzing a sample to determine the presence and/or amount of auto-antibodies against annexin A3 and optionally for the presence and/or amount of regulatory T-cells, and diagnosing a malignant condition where auto-antibodies against annexin A3 and optionally regulatory T-cells are present in said sample.

12. A method for the stratification of a subject which has been classified as having an intermediate risk of developing prostate cancer, comprising analyzing a tissue sample from said subject to determine intracellular distribution of annexin A3; and stratifying said subject as at high risk for a pre-malignant or malignant condition if the analysis is characterized by a diffuse intracellular localization of annexin A3 staining of said tissue sample of said subject compared to stratifying said subject as at low risk for a pre-malignant prostate condition where intracellular apical annexin A3 staining is detected in said tissue sample.

13. The method of claim 5, wherein said tissue sample is a biopsy.

14. The method of claim 6, wherein said epithelial cells are prostate epithelial cells.

15. The method of claim 11, wherein said sample is a tissue sample of a body fluid sample.

16. The method of claim 11, wherein said autoimmune response is characterized by the present of auto-antibodies against annexin A3 and/or prostasomes/exosomes or by the presence of ANXA3-positive regulatory T-cells.

* * * * *